United States Patent [19]
Holleman et al.

[11] Patent Number: 5,366,494
[45] Date of Patent: Nov. 22, 1994

[54] METHOD AND APPARATUS FOR IMPLANTATION OF DEFIBRILLATION ELECTRODES SYSTEM

[75] Inventors: Timothy W. Holleman, Ham Lake; Clare P. Ulrich, Minneapolis; Brian L. Fideler, Columbia Heights, all of Minn.

[73] Assignee: Medtronic, Inc., Minneapolis, Minn.

[21] Appl. No.: 56,282

[22] Filed: Apr. 30, 1993

[51] Int. Cl.⁵ ............................................. A61N 1/05
[52] U.S. Cl. .................................. 607/119; 607/122; 128/642
[58] Field of Search ............... 607/5, 37, 38, 116, 607/119, 122, 123, 125–128, 132; 128/642

[56] References Cited
U.S. PATENT DOCUMENTS

| 4,258,725 | 3/1981 | O'Neill | 607/37 |
| 4,466,690 | 8/1984 | Osypka . | |
| 4,951,687 | 8/1990 | Ufford et al. | 607/122 |
| 4,954,105 | 9/1990 | Fischer . | |
| 5,036,862 | 8/1991 | Pohndorf . | |
| 5,060,649 | 10/1991 | Hocherl . | |
| 5,174,303 | 12/1992 | Schroeppel | 128/642 X |

FOREIGN PATENT DOCUMENTS

| 0343402 | 11/1989 | European Pat. Off. | 607/37 |
| 3304506 | 8/1984 | Germany | 607/37 |
| 9219321 | 11/1992 | WIPO | 607/122 |

Primary Examiner—Lee S. Cohen
Assistant Examiner—Jeffrey R. Jastrzab
Attorney, Agent, or Firm—Reed A. Duthler; Harold R. Patton

[57] ABSTRACT

A method and apparatus for implantation of an electrode system. The apparatus includes a pacing lead and an extender, both of which are provided with internal stylet lumens. When coupled to one another, the stylet lumen of the extender is in communication with the stylet lumen of the lead, allowing passage of a stylet through both lead and extender, while coupled together.

4 Claims, 5 Drawing Sheets

METHOD AND APPARATUS FOR IMPLANTATION OF DEFIBRILLATION ELECTRODES SYSTEM

BACKGROUND OF THE INVENTION

This invention relates generally to medical electrical leads and more, particularly to implantable leads for use in cardioverting or defibrillating the heart.

Implantable cardioverters and defibrillators, as presently available, are of substantial size, with the result that in most cases the devices are implanted in the abdominal region, rather than in the pectoral region as typically employed for cardiac pacemakers. As a result, the distance from the defibrillator or cardioverter to the location of the electrode in the heart is substantially greater than would be the case in a corresponding pectoral implant. In systems employing transvenous leads, the leads are tunnelled subcutaneously for a substantial distance between the site of venous insertion to the device implant site.

In the context of cardiac pacing, abdominal implants of pulse generators have also been employed, and in some cases, in order to accommodate the increased distance between the pulse generator and the electrode in the heart, lead extenders have been employed. Typically, such extenders have included a receptacle at one end, for receiving the connector pin of the pacing lead and have employed a connector pin at the other end, corresponding to the connector pin of the pacing lead. For example, Medtronic, Inc. has manufactured and sold such lead extenders, Model Nos. 6981 and 6981M, for some time.

Lead extenders and similar devices have also been employed to repair previously implanted leads having broken or damaged connector pins and/or lead bodies. For example, such repair kits are illustrated in U.S. Pat. No. 5,036,862 issued to Pohndorf, U.S. Pat. No. 5,060,649 issued to Hocherl et al., U.S. Pat. No. 4,954,105 issued to Fischer and U.S. Pat. No. 4,466,690 issued to Osypka.

Generally, when lead extenders are employed, they are coupled to the electrode lead after its implantation within the heart. The lead extender is thereafter tunneled subcutaneously or otherwise routed through the body to the implantable pulse generator.

SUMMARY OF THE INVENTION

The present invention is directed toward an improved method and apparatus for implanting medical electrode leads of the type in which positioning of the electrode lead accomplished by means of an insertable styler, passed through the body of the lead. The invention is particularly adapted for use in circumstances where the device to which the electrode lead is to be connected is located remote from the site of venous insertion of the lead and for use in repairing damaged leads.

The present invention provides a lead extender to be used with the; electrode lead, which allows for passage of a stylet through the extender and into the body of the lead. Unlike previous extenders, the present extender allows the physician the option of manipulating the lead by means of stylet, after connection to the extender. The lead and extender may be provided to the physician pre-connected, with a long stylet employed during the initial implantation process or the lead and extender may be connected after initial implant, with a shorter stylet used for initial positioning of the lead. If repositioning after initial implant is desired, the physician has the option to access the lead at the implantation site of the device, and the long stylet may be used to manipulate the lead. Alternatively, if the junction of the lead and extender is located adjacent the site of venous insertion of the device, or other convenient location, the lead may be accessed at that location, disconnected from the extender, and the shorter stylet may be used to reposition the lead.

The present invention may also be used as a repair kit to provide a replacement or substitute connector for previously implanted leads. If so employed, the cut end of the lead is inserted into the extender, rather than the connector pin on the lead. In this use, the extender retains the advantage of allowing passage of a stylet into the previously implanted lead, a feature absent from the prior art lead repair devices as discussed above.

DETAILED DESCRIPTION OF THE PREFERRED EMBODIMENTS

Figure 1:
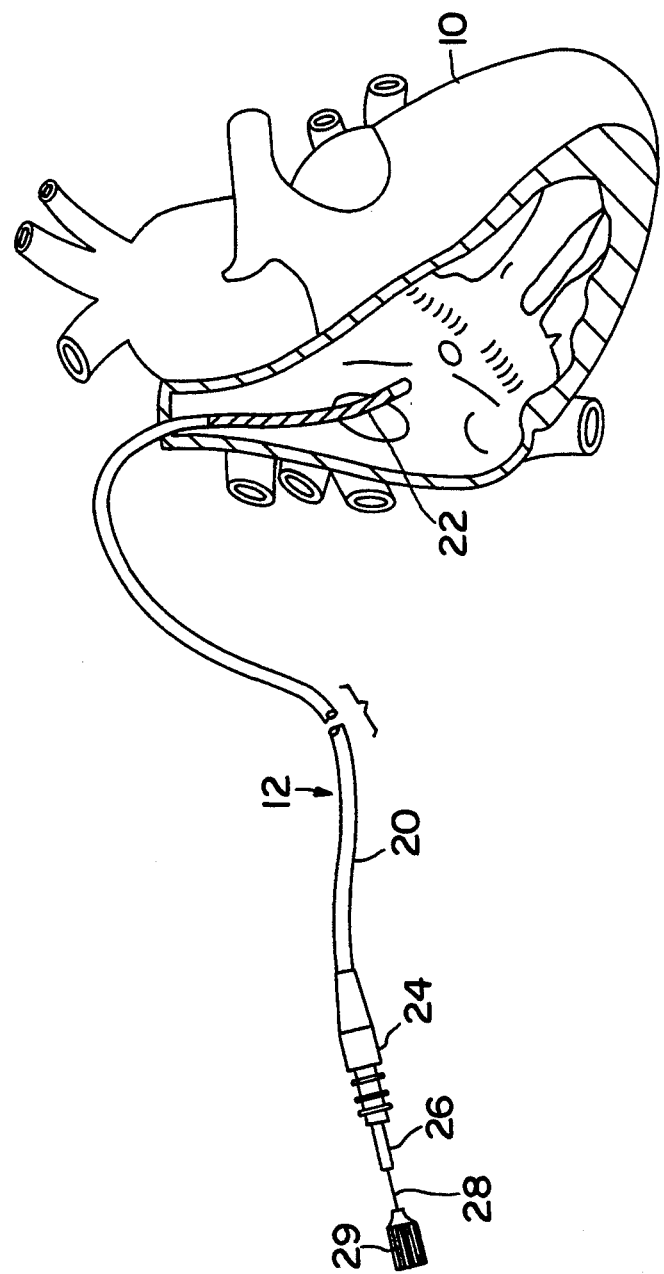
FIG. 1 is a cutaway view of the heart and a cardioversion or defibrillation electrode lead, illustrating the passage of a short stylet therethrough to manipulate the lead.

FIG. 1 shows a cutaway view of a human heart, illustrating the entry of the distal end of defibrillation lead 12 into the right atrium via the superior vena cava. The defibrillation lead is provided with an elongated defibrillation electrode 22, mounted adjacent the distal end of the insulative lead body 20. At the proximal end of the lead is a connector assembly carrying a conductive pin 26. Pin 26 is coupled to electrode 22 by means of a coiled conductor located within lead body 20. Stylet 28 is inserted through a central lumen in pin 26, and passed through the central lumen defined by the conductor coil within lead body 20 to a point adjacent the distal end of the lead. A knob 29 located on the proximal end of the stylet 28 allows for manipulation of the stylet.

The stylet 28 may be either a straight or curved wire, and is used to guide the electrode 22 to its desired location within the heart. For example, the location may be as illustrated, in the right atrium and/or superior vena cava or the lead may be further advanced into the coronary sinus or right ventricle of the heart. The initial implantation of the lead 12 as illustrated corresponds to implantation of such leads, as generally practiced in the prior art, and lead 12 may be considered equivalent to any transvenous cardiac pacing, defibrillation or cardioversion lead having a stylet lumen, for purposes of the present invention.

Figure 2:
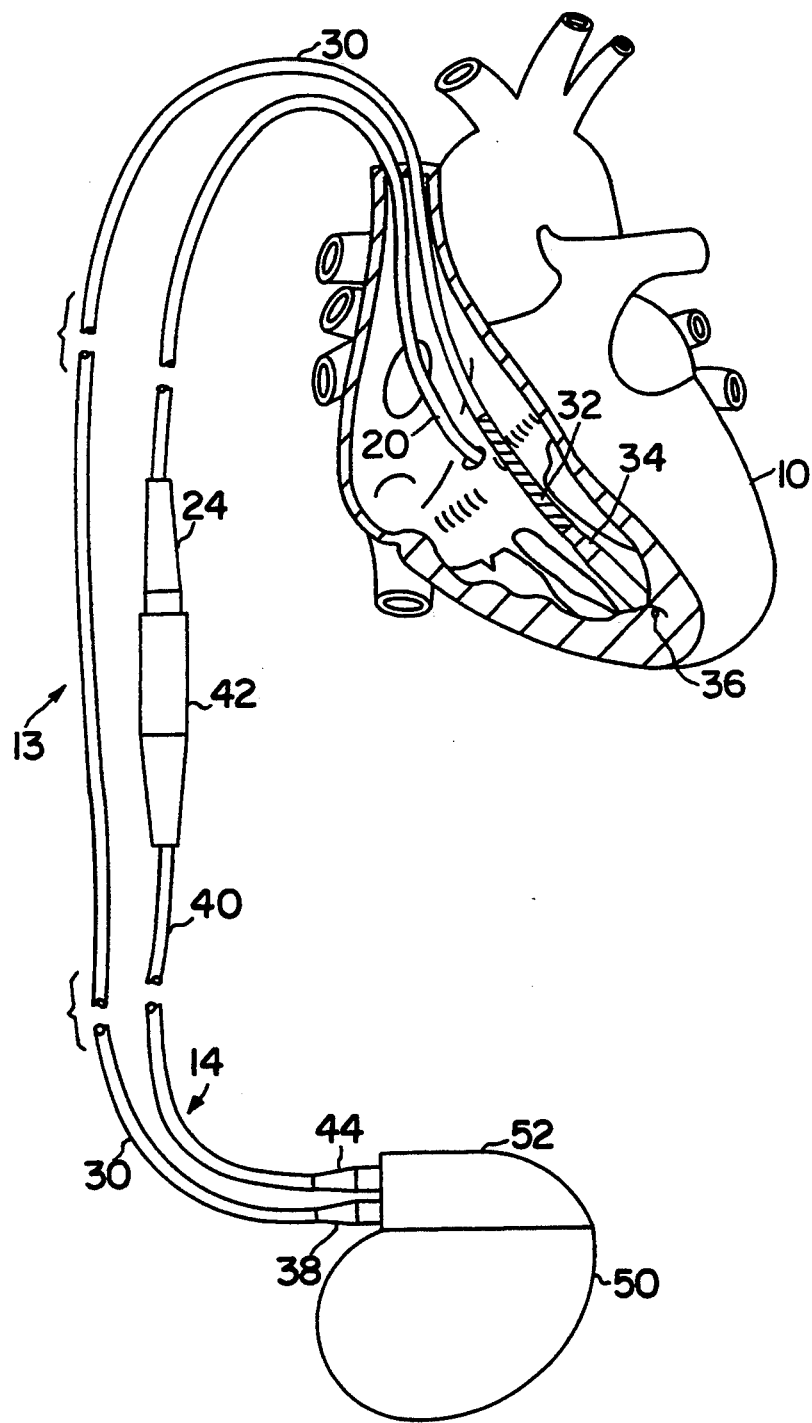
FIG. 2 is a cutaway view of the heart, in conjunction with a plan view of an implantable cardioverter or defibrillator and a cardioversion or defibrillation lead system employing the present invention, as implanted.

FIG. 2 illustrates the interconnection of lead 12 with a lead extender 14, a second electrode lead 13, and an implantable pacemaker/cardioverter/defibrillator 50, as ultimately implanted. The connector assembly 24 is inserted into a receptacle 42 mounted on the proximal end of the insulative lead extender body 40. The conductive pin 26 (FIG. 1) is electrically coupled to a corresponding connector block within receptacle 42, which connector block is in turn coupled to an elongated coil located within the extender body 40, terminating in a connector assembly 44, which is inserted into one of the bores of connector housing 52. The connector pin of connector assembly 44 is coupled to an internal connector block within connector housing 52, and thereby is coupled to the circuitry of the implantable pacemaker/cardioverter/defibrillator 50. The connector pin on connector assembly 44, the connector block within receptacle 42 and the conductor coil within extender body 40 are all provided with communicating stylet lumens, allowing the passage of a stylet through extender 14 and into lead 12.

Also illustrated is a second transvenous defibrillation lead 13, provided with an elongated defibrillation electrode 32 located adjacent the distal end of insulative lead body 30 and with pacing and sensing electrodes 34 and 36. As illustrated, lead 13 is approximately the length of the lead 12 and the extender 14, taken together. Within lead body 30 are three coaxially arranged, mutually insulated coiled conductors, coupled to implantable pacemaker/cardioverter/defibrillator 50 by means of a multi-contact connector assembly 38, which is in turn inserted into connector housing 52 and is coupled to three connector blocks therein. While not so illustrated, the present invention is also believed practicable in the context of a multiple electrode lead such as lead 13.

As connected, electrodes 32 and 22 (FIG. 1) are coupled to the output of the cardioversion/defibrillation pulse generator circuitry within pacemaker/cardioverter/defibrillator 50. Electrodes 34 and 36 are coupled terminals of the sense amplifier within pacemaker/cardioverter/defibrillator 50 as well as being coupled to the output of the pacing pulse generator therein. Electrodes 34 and 36 are employed for sensing cardiac rhythms, including the sensing of tachyarrhythmias to trigger delivery of defibrillation and cardioversion shocks. Electrodes 34 and 36 are also employed for bradycardia and antitachycardia pacing.

Figure 3:
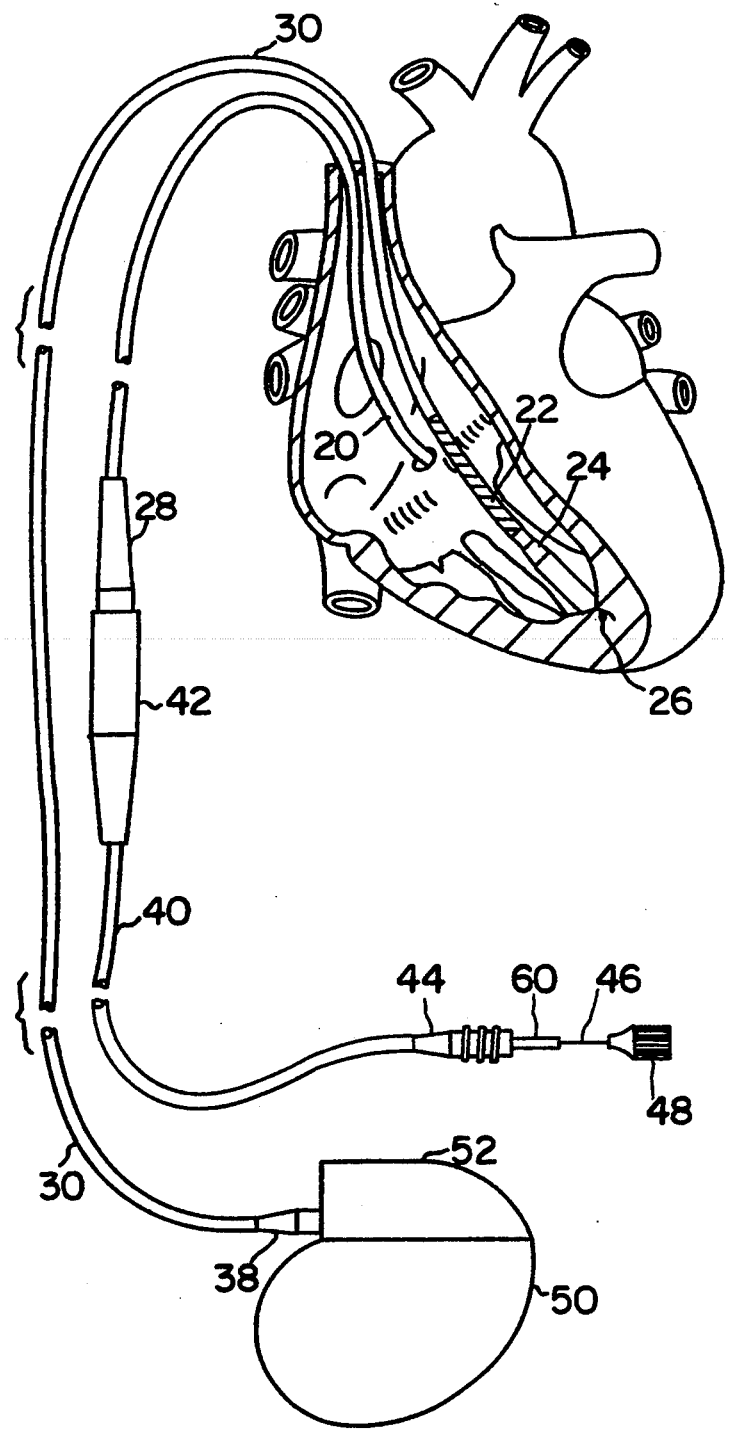
FIG. 3 is a cutaway view of the heart, in conjunction with a plan view of a cardioversion or defibrillation lead system employing the present invention, illustrating passage of a longer stylet through the extender and lead to manipulate the lead.

FIG. 3 illustrates the same system as shown in FIG. 2, with all labelled elements corresponding to identically labelled elements in FIG. 2. As illustrated, the connector assembly 44 located at the proximal end of lead extender body 40 has been removed from connector housing 52, allowing insertion of an elongated stylet 46, which is sized to be able to pass through the connector pin 60, through the coiled conductor within the body of lead 40, through the coiled conductor within extension 40, through the pin 26 (FIG. 1) of lead 20, down to a point adjacent the distal end of lead 20, so that the elongated stylet 46 may be employed to adjust the position of electrode 22 (FIG. 1) on lead 20, without disconnecting the extender 40 from lead 20.

For example, in the context of an implantable defibrillator, leads 12 and 13 may enter the venous system through the left or right subclavian or cephalic vein, in the left or right pectoral region of the body, and extend distally into the heart. The leads in this context would extend proximally toward the abdomen, tunneled subcutaneously to the abdominal implant site of implantable pacemaker/cardioverter/defibrillator 50. The junction of the extender 14 and the lead 12 may be located subcutaneously in between the two operative sites, and thus may not readily be accessible. Alternatively, the junction may be located adjacent the site of venous insertion.

Figure 4:
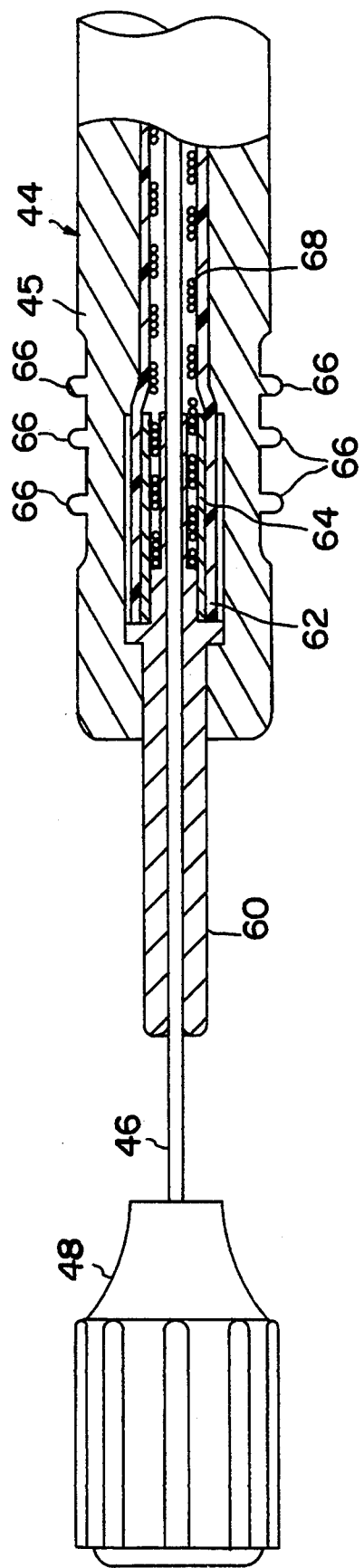
FIG. 4 is a cutaway view through the proximal end of the lead extender.

FIG. 4 is a cutaway view through the connector assembly 44 of extender 14. The connector assembly 44 includes an outer sleeve 45 molded of a resilient insulative plastic such as polyurethane or silicone rubber and provided with three sealing rings 66, which seal the connector assembly 44 within the bore of a connector housing located on an implantable device such as a pulse generator or implantable pacemaker/cardioverter/defibrillator. Extending proximally from connector assembly 44 is metal connective pin 60 which is coupled to conductive coil 68 by means of a crimping sleeve 64, compressed to mechanically couple coil 68 to the distal end of pin 60. Surrounding coiled conductor 68 is an elongated insulative sleeve 62 which comprises the exterior of the lead body 40 (FIG. 2) and extends until the receptacle 42, located at the distal end of the extender 40. As illustrated, a stylet 46, provided with knob 48 passes through an internal lumen within pin 60, which is in communication with the interior lumen of coiled conductor 68. Stylet 46, as illustrated in FIG. 3, may pass through the entire length of extender 40 and through the entire length of the lead coupled to extender 40. FIG. 4 is also illustrative of the structure of a type of connector assembly of implantable leads for use with the extender 14.

Figure 5:
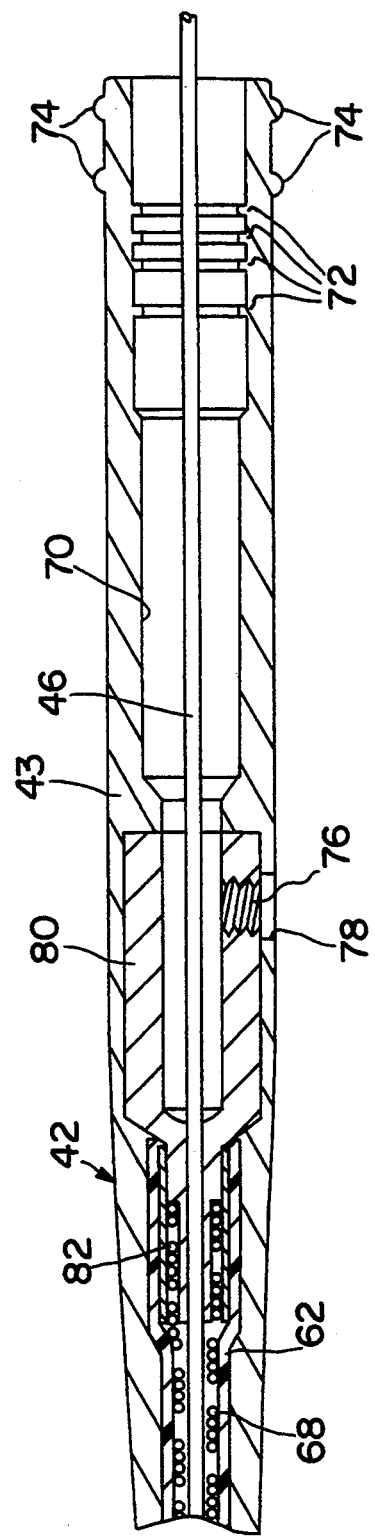
FIG. 5 is a cutaway view through the distal end of the lead extender.

FIG. 5 is a cutaway view through a receptacle 42 mounted to the distal end of lead extender 14. Coiled conductor 68 is coupled to a conductive connector block 80, by means of a crimping sleeve 82, mechanically compressing coil 60 against the proximal extension of connector block 80. Insulative sleeve 62 terminates within connector assembly 42.

Receptacle 42 includes a molded outer sleeve 43, which may be fabricated of silicone rubber, polyurethane, or other implantable plastic. Sleeve 43 is provided with an internal lumen 70, aligned with the internal lumen of connector block 80 and is provided with inner sealing rings 72 and circumferential ridges 74, between which a tightening suture may be tied to further seal the interior of lumen 70 against the connector assembly of the lead to be inserted into receptacle 42. Connection of the connector block 80 to a connector pin, such as connector pin 26, FIG. 1, is accomplished by means of a set screw 76 accessible through port 78. After tightening, port 78 will typically be filled with medical adhesive to provide a fluid seal.

As can be seen from the illustration of FIG. 5, stylet 46 passes through a lumen in the proximal extension of connector block 80, and is centered within the bore of connector block 80, so that it will align with the corresponding bore and the connector pin, (e.g., pin 26) of the lead to be inserted into lumen 70, allowing for passage of stylet 46 through both the lead and the extender.

When the extender 14 is used to repair a damaged lead, for example a lead having a connector assembly generally as illustrated in FIG. 4, typically the connector assembly and any adjacent damaged portion of the lead will be removed. Thereafter and a length of the outer insulation (which may correspond to sleeve 62) will be removed from the coiled conductor (which may correspond to conductor 68). An insulative sleeve may be placed around the remaining outer insulation, adjacent the bare conductor the conductor then inserted into connector block 80 and then retained by means of set screw 78. Additional sealing of the lead to the receptacle 42 may be provided by means of medical adhesive.

As discussed above, the present invention provides an enhanced set of available implantation, manipulation and repair techniques for use in conduction with implantable medical leads of the type having stylet lumens. Initial electrode positioning may be accomplished by means of a relatively short lead and stylet in combination, which is more convenient for the physician than a corresponding longer lead and stylet combination, followed by connection of the lead to the extender. Thereafter, repositioning may be accomplished without requiring disconnecting the extender. Alternatively, initial electrode location may be accomplished using the lead and extender already connected and a longer stylet, avoiding the necessity of the physician having to connect the two devices, while still allowing repositioning thereafter by accessing the junction of the extender and lead, if more conveniently located, e.g. adjacent the site of venous insertion. Depending upon the particular application for the lead and extender, the physician may choose either of the implantation techniques. In the context of use of the extender as a repair kit, the extender provides the opportunity to reposition the lead after the repair, rather than foreclosing this possibility as in the above-cited repair devices.

While the above disclosure illustrates the present invention in a context of an implantable cardioversion and defibrillation lead system, the present invention may also be employed in the context of other type of implantable electrical leads, for example including nerve and muscle stimulating electrodes, as well as cardiac pacing electrodes. Further, as discussed above, while the above disclosure illustrates the present invention in the context of a unipolar lead having a single coiled connector, the invention may also be practiced in the context of leads of other types. Including leads having multiple conductors as well as leads having conductors of other types, so long as a styler lumen is provided, which may be correspondingly aligned to a stylet lumen in the associated lead extender. As such, the above disclosure should be considered as exemplary, rather than limiting, with regard to the scope of the claims which follow:

I claim:

1. An implantable medical lead system, comprising:
   a medical electrical lead having an elongated lead body, an electrode located along said lead body, a first connector assembly mounted to a proximal end of said lead body, a first conductor coupling said electrode to said first connector assembly, and a first stylet lumen extending from said first connector assembly to a point adjacent said electrode;
   a lead extender mounted to said medical electrical lead, said extender having an elongated body, a receptacle having means for coupling to said first connector assembly, said lead extender being mounted to a distal end of said elongated lead body, a second connector assembly mounted to a proximal end of said lead body, a second conductor coupling said receptacle to said second connector assembly, and a second stylet lumen extending from said second connector assembly to said receptacle, said coupling means of said receptacle being coupled to said first connector assembly on said lead, such that said first and second stylet lumens communicate with one another allowing passage of a stylet through both said first and second lumens; and
   an elongated stylet removably inserted within said first and second stylet lumens, extending from said first connector assembly to a point adjacent the distal end of said lead.

2. A lead system according to claim 1 wherein said first and second conductors comprise elongated coils having said first and second stylet lumens extending therethrough.

3. A method of positioning a medical electrical lead having a stylet lumen, comprising:
   connecting said lead to a lead extender having a stylet lumen;
   inserting a stylet into the stylet lumens of said lead and said extender;
   locating said lead in a desired location by manipulating said stylet.

4. A method according to claim 3 wherein said locating step comprises locating said lead in a patient's heart after said connecting and inserting steps.

* * * * *